(12) United States Patent
Magnusson

(10) Patent No.: US 6,931,283 B1
(45) Date of Patent: Aug. 16, 2005

(54) IMPLANTABLE TISSUE STIMULATING DEVICE

(75) Inventor: Gunnar Magnusson, Arsta (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 09/914,248

(22) PCT Filed: Feb. 1, 2000

(86) PCT No.: PCT/SE00/00203

§ 371 (c)(1),
(2), (4) Date: Aug. 24, 2001

(87) PCT Pub. No.: WO00/50120

PCT Pub. Date: Aug. 31, 2000

(30) Foreign Application Priority Data

Feb. 25, 1999 (SE) .................................. 9900682

(51) Int. Cl.⁷ ................................................ A61N 1/18
(52) U.S. Cl. ...................................................... 607/36
(58) Field of Search ................................. 607/36, 9, 4

(56) References Cited

U.S. PATENT DOCUMENTS

| 3,971,388 | A |  | 7/1976 | Cowdery |
| 4,071,032 | A |  | 1/1978 | Schulman |
| 4,094,321 | A |  | 6/1978 | Muto |
| 5,476,496 | A |  | 12/1995 | Strandberg et al. |
| 5,480,416 | A |  | 1/1996 | Garcia et al. |
| 5,535,097 | A |  | 7/1996 | Ruben et al. |
| 5,658,321 | A |  | 8/1997 | Fayram et al. |
| 5,662,692 | A |  | 9/1997 | Paspa et al. |
| 5,876,424 | A | * | 3/1999 | O'Phelan et al. ............. 607/36 |

* cited by examiner

Primary Examiner—Mark Bockelman
(74) Attorney, Agent, or Firm—Schiff Hardin LLP

(57) ABSTRACT

A housing for an implantable tissue stimulating device is connectable to an electrode lead having an electrode. A portion of the housing also functions as an electrode. The walls of the housing are shaped so that when a voltage is applied between the electrode at the electrode lead, and the housing electrode, the electric field associated with the voltage has a low field strength in regions at which unwanted stimulation of muscles can occur.

13 Claims, 3 Drawing Sheets

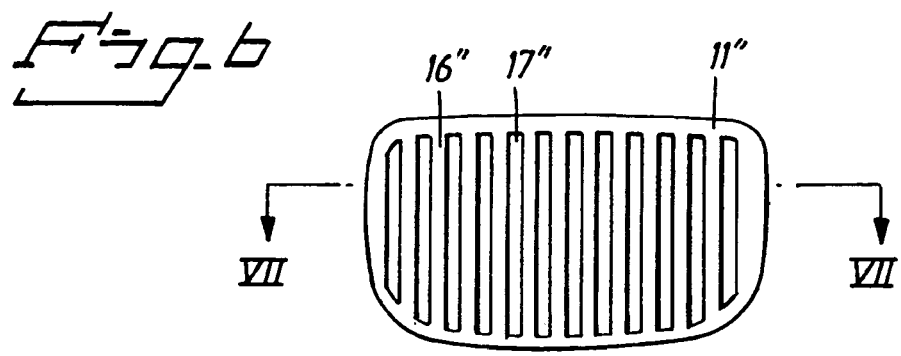
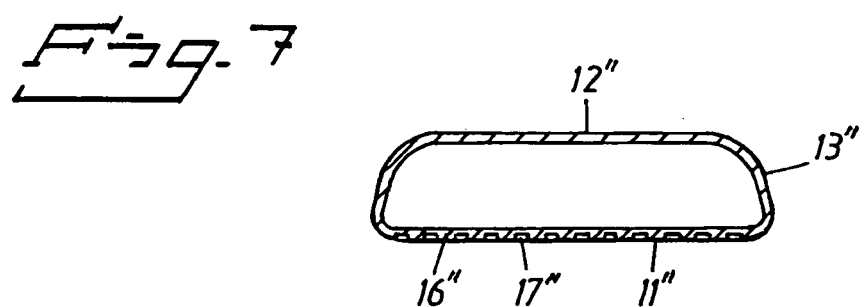
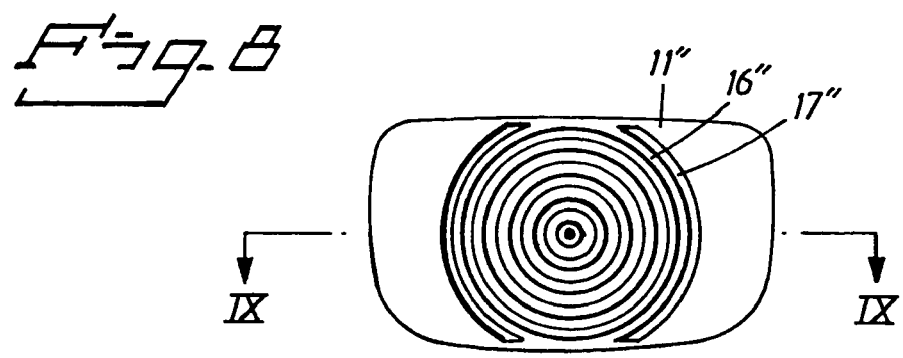
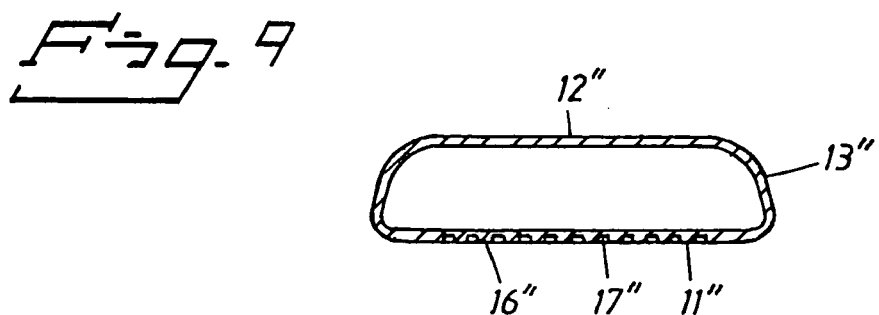

IMPLANTABLE TISSUE STIMULATING DEVICE

BACKGROUND OF THE INVENTION

1. Field of the Invention

The invention relates to a housing for an implantable tissue stimulating device, especially an implantable heart stimulation device.

2. Background of the Invention and Related Art

Heart stimulation devices for human beings, such as pacemakers are usually implanted in the chest, generally on the left side, a short distance below the clavicle or collar bone. The device will then rest between the pectoralis major and the skin. An electrode lead supplies electric pulses to the heart from the device. The electrode lead includes one or more electrodes, a connector at the proximal end of the electrode lead for connection of the lead to the stimulation device conductor(s) between the connector pin and the electrode(s), one of which typically is located at the distal end of the lead and insulation. The electrode lead is typically passed upwardly over the clavicle and is connected to the heart through a vein adjacent to the clavicle. Usually, the housing of the heart stimulating device is made of conductive material, and electric pulses to the heart are delivered by means of a distal electrode of the electrode lead, being located in the heart in electrical contact with the tissue. The housing is implanted so as to be in electrical contact with the surrounding tissue, and constitutes a second electrode surface. The object is to create an electrical field at the interface of the distal electrode of the electrode lead (stimulation electrode) with the underlying myocardium. However, in a device as described, an electrical field will also be created between the stimulation electrode and the housing. This may, depending on the strength of the field, cause unwanted stimulation of other muscles subjected to the field, e.g. the pectoralis major. To avoid this effect, parts of the housing can be provided with an insulating cover, e.g. of parylene. Usually the whole housing except for a contact window in a central portion of the side of the housing facing the skin, when implanted, is covered with parylene. In such a case the electric field from the housing will be concentrated to the area of the window.

U.S. Pat. No. 5,480,416 refers to such devices as prior art, and further discloses a pacemaker having two sides covered with parylene, while an edge joining the two sides is uninsulated, and constitutes a contact surface. Thus this pacemaker can be implanted with either of its two sides facing the skin of its carrier.

U.S. Pat. No. 5,658,321 discloses an implantable defibrillator or pulse generator having an electrically conductive housing used as an electrode. The exterior surface of the housing is provided with ridges. Hereby the surface area is increased, and the electrical resistance in the housing/tissue interface is decreased. By the arrangement of sharp corners in connection with the ridges, a further resistance reduction is achieved.

A further casing for a power supply and pulsation control circuitry of a cardiac pacer is disclosed in U.S. Pat. No. 4,094,321. This casing has a substantially flat bottom surface and a shallow dome-shaped top, which tapers to a thin peripheral edge of a small radius of curvature juxtaposed to the bottom and merging curvelinearily therewith. The substantially flat bottom surface can be of metal, epoxy or other suitable inert coating. Further, the bottom surface is provided with a catheter storage means, including rims or grooves. When implanted the casing is located with the dome-shaped top facing the skin, and the substantially flat surface supported by muscles or ribs.

The method widely used today for preventing generation of electric fields in regions where they could cause unwanted stimulation of muscles, by covering portions of a housing, which serves as an electrode, with an insulating material such as parylene, is an effective method. However, it is costly due to the step of the application of the parylene itself and the pre-treatment and after treatment steps.

SUMMARY OF THE INVENTION

It is an object of the invention to provide a housing for an implantable tissue stimulating device which allows the electric fields, which are generated around the housing and which could cause unwanted muscle stimulation, to be eliminated or at least reduced to a safe level, so the risk of unwanted muscle stimulation is eliminated, and which can be produced in a simpler and more cost-effective manufacturing process.

The above object is achieved in accordance with the principles of the present invention in a housing for an implantable tissue stimulating device that has a first wall adapted to face the skin of a patient, when the housing is implanted, the first wall having a first generally flat exterior surface, a second wall having a second generally flat exterior surface and a circumferential third wall joining the first and second walls and having a curved first circumferential wall section connected to the first wall and a curved second circumferential wall section connected to the second wall. The third wall is made of conductive material which is adapted to be in electrical contact with surrounding tissue and to serve as an electrode. The radius of curvature of the first wall section is smaller than the radius of curvature of the second wall section with regard to curve radii in respective planes substantially perpendicular to the first and second flat surfaces. The housing is connectable to an electrode lead, and when a voltage is applied between the housing and the electrode of the electrode lead, an electric field is obtained having a lower fields strength along the curved second circumferential wall section than along the curved first circumferential wall section.

The inventive housing for an implantable tissue stimulating device, when implanted, acts as an electrode and shaped so as create low strength electric fields in regions where unwanted stimulation of muscles can occur, without the need top cover portions of the housing with an insulating layer.

By the arrangement of a curved circumferential first wall section connected to a first wall having a generally flat exterior surface, and a curved circumferential second wall section connected to a second wall having a generally flat exterior surface, where the first wall section has a smaller radius of curvature than the second wall section a favorable electric field distribution around the housing is obtained.

Roughening the surface or providing the surface with ridges or irregularities can increase the electrical field at the region of the wall facing the skin.

BRIEF DESCRIPTION OF THE DRAWINGS

FIG. 6 is a schematic view of an alternative surface structure of the first wall of the housing of the invention.

FIG. 7 shows a cross section taken at VII—VII in FIG. 6.

FIG. 8 is a schematic view of a further alternative surface structure of the first wall of the housing of the invention.

FIG. 9 shows a cross section taken at IX—IX in FIG. 8.

DESCRIPTION OF PREFERRED EMBODIMENTS

Figure 1:
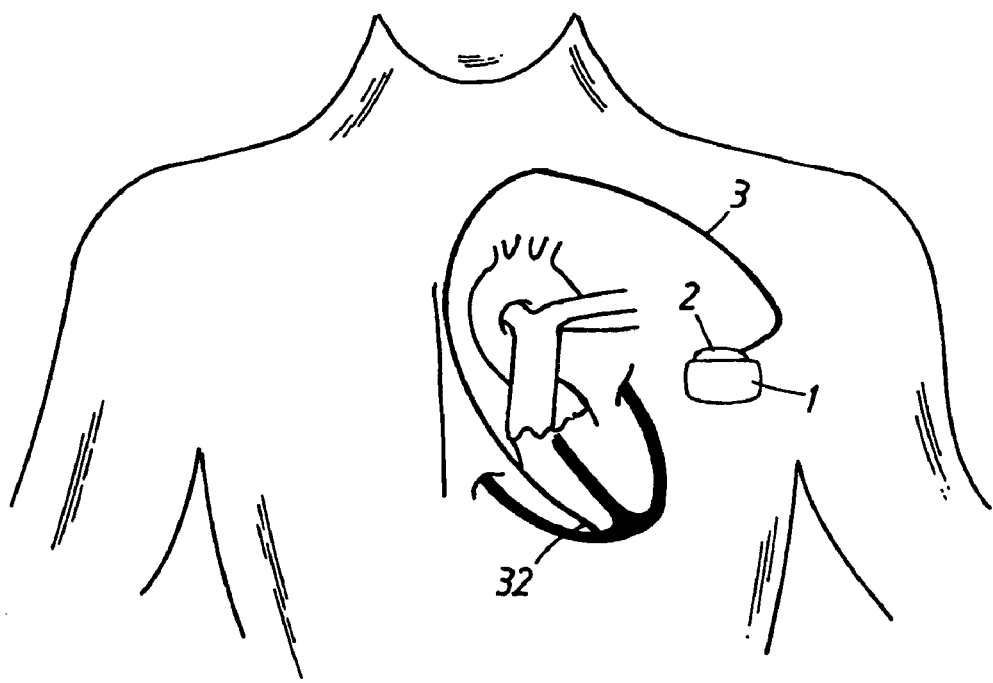
FIG. 1 schematically shows a pacemaker implanted in a patient.

A conventional placement of a pacemaker implanted in a patient is shown. A housing 1 for a pulse generator is implanted on the left side of the chest. The housing is conductive, made of a bio-compatible material such as titanium, and hermetically sealed against intrusion of body fluids and tissue when implanted. On top of the housing a header 2 is arranged. The header is made of transparent epoxy resin, and is molded onto the housing. The header includes a female portion of an electrical connector coupled to the circuits of the pulse generator. An electrode lead 3 includes at its proximal end a male connector 31 (connector pin, not shown) for electrical connection with said female connector. At the distal end the electrode lead 3 is provided with a stimulation electrode 32, which is located in the heart in electrical contact with the tissue. A stimulation pulse generated by the pulse generator will be applied between the electrode 32 and the housing 1, which also acts as an electrode. The electrode 32 may also serve as a sensing electrode, and the housing 1 then serves as the second sensing electrode. Between the male connector 31 and the electrode 32 the lead 3 includes an electrically conductive wire provided with insulation.

Alternatively the lead may have an additional electrode, preferably also located in the heart. In such a case, sensing is preferably performed by means of the electrodes of the lead, and the number of insulated wires of the lead will be the same as the number of the electrodes.

Figure 2:
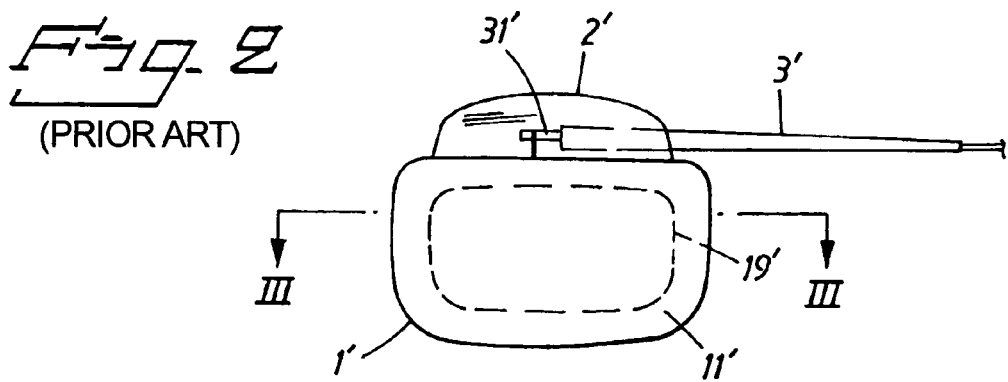
FIG. 2 is a schematic view of a prior art pacemaker.

In FIG. 2, the housing and a proximal lead portion of a prior art device to be implanted as shown in FIG. 1, is shown in an enlarged view. The housing 1' has a first wall 11' having a first generally flat exterior surface. The housing is adapted to be implanted with this first surface facing the skin of the patient.

Figure 3:
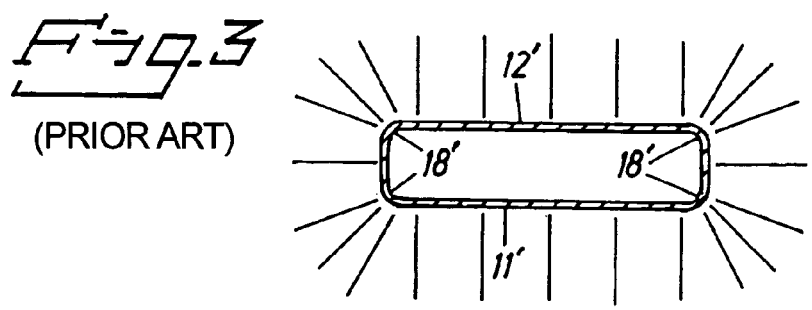
FIG. 3 shows a cross section taken at III—III in FIG. 2.

FIG. 3 is a cross section taken at III—III in FIG. 2, with the housed parts and components omitted, for simplicity. Opposed to the first wall 11', a second wall 12' having a second generally flat exterior surface, is provided. The first and second walls 11', 12' are joined by a connecting wall, and corners 18' are formed where the connecting wall joins the first wall 11' and the second wall 12', respectively. When a voltage is applied between the electrode of the lead and the housing, an electric field will bee generated around the housing. This is illustrated with schematic field lines. Along the corners 18' the field will exhibit strong field concentrations, leading to high current densities in the surrounding tissue and possibly to unwanted stimulation of muscles. To prevent this, prior art devices have been provided with an insulating parylene coating of the whole housing except for a central portion of the surface facing the skin of the patient, as mentioned above. This portion or window 19' is shown with broken lines in FIG. 2.

Figure 4:
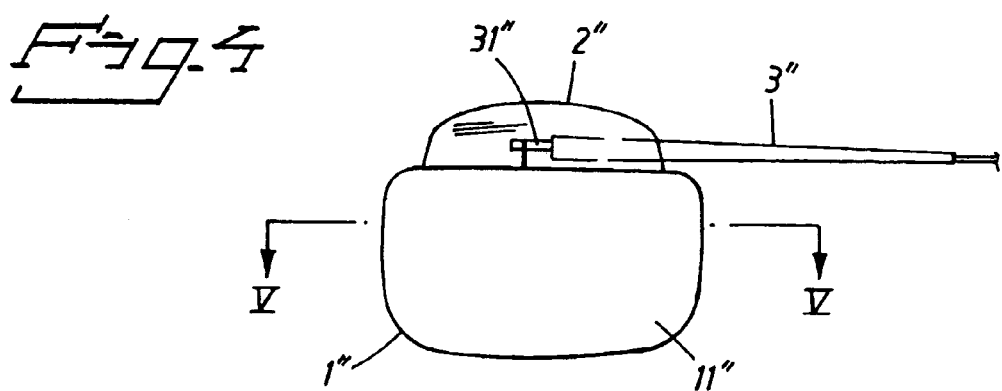
FIG. 4 is a schematic view of an embodiment of a housing for an implantable tissue stimulating device according to the invention.
Figure 5:
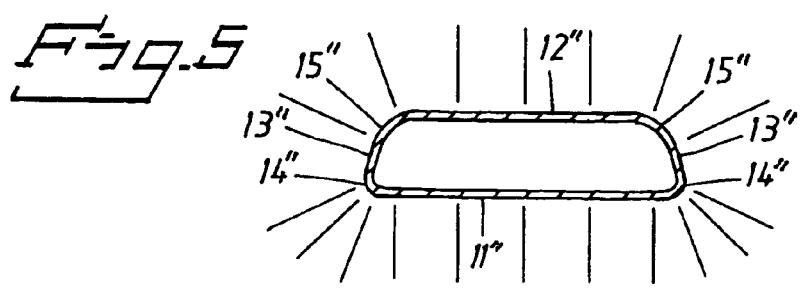
FIG. 5 shows a cross section taken at V—V in FIG. 4.

An embodiment of a housing for an implantable tissue stimulating device according to the invention is shown in FIG. 4, and a cross section taken at V—V thereof is shown in FIG. 5. This device is also adapted to be implanted as shown in FIG. 1. Also in FIG. 5 the housed parts and components are omitted, for simplicity. A housing 1" has a first wall 11", having a first generally flat exterior surface, and a second wall 12" having a second generally flat exterior surface. The first and second walls 11', 12" are joined by a third circumferential wall 13". The third wall 13" has a curved circumferential first wall section 14" that is connected to the first wall 11" around its periphery. The third wall 13" further has a curved circumferential second wall section 15" that is connected to the second wall 12".

On top of the housing 1" a header 2" is provided. It is of the above mentioned kind, made of transparent epoxy, and molded onto the housing 1". The header 2" could be molded to the housing 1" so as to cover an adjacent portion of the second wall section 15" and possibly also an adjacent portion of the first wall section 14".

The first wall 11', second wall 12" and third wall 13" are all made of an electrically conductive material, such as titanium, and the housing is hermetically sealed.

As seen in FIG. 5 the radii of curvature of the first wall section 14" and the second wall section 15", taken in a plane perpendicular to the first 11" and second 12" walls, are different. The first wall section 14", has a smaller radius of curvature, whereas the second wall section 15" has a greater radius of curvature. The ratio between the curve radii is in the range of 1:2–1:6, and preferably around 1:4. When discussing the radii of curvature of the wall sections, it is assumed that the thicknesses of the wall sections are uniform. However, this is not necessary, and in cases where a curve radius of a wall section is difficult to define it is referred to the exterior surface of the actual wall section.

The condition that the first wall section 14" has smaller radius of curvature than the second wall section 15" is generally valid for all planes through and perpendicular to the first and second walls 11", 12". Preferably the ratio between the radii of curvature is the same all the way along the third wall 13". However, in the region of the header, the desired effect could be obtained due to the insulating properties of the header material, especially when the header covers a portion of the second wall section 15". In such a case the relation between the radii of curvature at this location can be somewhat different than mentioned above, without departing from the spirit of the invention.

The first and second wall sections 14", 15" are circularly curved in said planes. For a housing shown in FIG. 5, having a thickness of e.g. about 6 mm, i.e. the distance between the exterior surfaces of the first and second walls, the radii of curvature could bee 1 mm and 4 mm for the first and second wall sections 14", 15", respectively. However, the wall sections may be curved in other shapes, e.g. partially elliptical. It is important that the curve of the first wall section 14" is sharper than the curve of the second wall section 15". For housing thicknesses of e.g. 8 and 9 mm, the radii of curvature could be the same as for the 6 mm case. Practically the smallest radius of curvature (of the first wall section 14") should not be smaller than about 1 mm, even if it could be a sharp corner.

The housing shown in FIGS. 4 and 5 is adapted to be implanted in a patient with the first wall 11" facing the skin. When in use, and when pulses are applied to the stimulation electrode(s) of the electrode lead, an electric field is generated around the housing 1", which is coupled to the pulse generator, and acts as an electrode. By the arrangement of the curved circumferential first wall section 14" and the curved circumferential second wall section 15" where the first wall section 14" has smaller radius of curvature than the second wall section 15", a favourable electric field distribution around the housing is obtained. As illustrated in FIG. 5 with schematic field lines, there will be a lower field concentration in the region around the more smoothly curved second wall section 15" than in the region around the more sharply curved first wall section 14". Due to the weak electric field in the region around the curved second wall section 15" the current density here will be low, and the risk of unwanted stimulation is eliminated or at least heavily reduced. In the region around the curved first wall section 14", on the other hand, the electric field will be relatively strong, resulting in a relatively high current density in the adjacent tissue. This is advantageous since in this region there are no muscles that could be stimulated, and the currents can be distributed in a favorable way.

In order to smoothen the exterior surfaces of the second wall and second wall section, they can be polished. Thus small field concentrating irregularities of the surfaces are removed. This will homogenize the field, and possibly also reduce it. For the exterior surface of the first wall and possibly also for the first wall section the contrary is desired. Therefore the generally flat exterior surface of the first wall and possibly also the first wall section could be blasted in order to achieve a relatively rough surface. Besides a concentration of a field, a decreased electrical resistance in the housing/tissue interface around this wall and wall section is also achieved. Grinding, abrading, brushing, or chemically etching the surface e.g. to generate sharp peaks, which may be elongated ridges, could also form the roughness or irregularities of the surface(s) or individual pointed peaks.

FIG. 6 shows the exterior surface of the first wall 11" being roughened, textured or contoured. The exterior surface of the first wall 11" is provided with an array of grooves 17". The grooves 17" alternate with an array of ridges 16", each of which proceeds between and defines adjacent grooves. The grooves can be formed as mentioned above or by cutting, milling, or stamping. As an example, the grooves can be cut to a depth of 0.25 mm and a width of 0.40 mm, while the ridges have a width of 0.40 mm.

In FIG. 7 a cross section taken at VII—VII in FIG. 6, is shown. Here, the ridges 16" and grooves 17" are shown somewhat enlarged. The ridges are shown to be rectangular in cross section, however, they could have V-shaped cross-section.

FIG. 8 shows an alternative shape of the grooves 17" and ridges 16". Here they are formed in an annular and concentric pattern. Other patterns are also possible, e.g. elliptic or spiral. In FIG. 9 a cross section taken at IX—IX in FIG. 8, is shown. Also here, the ridges 16" and grooves 17" are shown somewhat enlarged. The cross-sectional shapes of the grooves and ridges could be the same as in the embodiment of FIGS. 6 and 7.

In the embodiments of the invention above, the first 11", second 12" and third 13" walls are all made of an electrically conductive material that is to be in contact with surrounding tissue. However the third wall 13" could be made of an electrically conductive material, and the second wall 12" and possibly also the first wall 11" made of a non-conductive material, or alternatively covered with an insulating layer.

The curve radii of the irregularities or ridges are very small, at least smaller than 1 mm, and they could be as small as 0.1 mm, or smaller.

Although the invention is described by means of the above examples, naturally, many variations are possible within the scope of the invention.

What is claimed is:

1. A biocompatible housing for an implantable tissue stimulating device having an electrode lead with an electrode: said housing being adapted for connection to said electrode lead and said stimulating device generating a voltage between said housing and said electrode, said voltage having an electric field associated therewith, said housing comprising:
   a first wall having a generally flat first exterior surface, said first wall being adapted to face the skin of a patient when said housing is implanted;
   a second wall having a generally flat second exterior surface; and
   a circumferential third wall joining said first wall and said second wall, said third wall being composed of conductive material and adapted for electrical contact with surrounding tissue when said housing is implanted to serve as an electrode, said third circumferential wall having a curved first circumferential wall section connected to said first wall and a curved second circumferential wall section connected to said second wall and substantially opposing circumferential wall portions between said curved first and second wall sections, said first circumferential wall section having a radius of curvature smaller than a radius of curvature of said second wall section, for curve radii in planes substantially perpendicular to said first surface and said second surface, causing said electric field to have a lower field strength along said second circumferential wall section than along said first circumferential wall section and a spacing between the first wall and second wall being less than a spacing between said substantially opposing wall portions of the circumferential third wall.

2. A housing as claimed in claim 1 wherein said first wall is composed of conductive material and is adapted to be an electrical contact with surrounding tissue for serving as an electrode in combination with the electrode formed by said third wall.

3. A housing as claimed in claim 1 wherein said second wall is composed of conductive material and is adapted to be an electrical contact with surrounding tissue for serving as an electrode in combination with the electrode formed by said third wall.

4. A housing as claimed in claim 1 wherein each of said first circumferential wall section and said second circumferential wall section is circularly curved in said planes.

5. A housing as claimed in claim 4 wherein said first circumferential wall section has a center of curvature along a continuous first curve, and wherein said second circumferential wall section has a center of curvature along a continuous second curve.

6. A housing as claimed in claim 5 wherein said first curve and said second curve are substantially parallel.

7. A housing as claimed in claim 1 wherein the respective curve radii of said first circumferential wall section and said second circumferential wall section in said planes is in a range between 1:2 and 1:6.

8. A housing as claimed in claim 7 wherein said ratio is approximately 1:4.

9. A housing as claimed in claim 1 wherein said first surface is rough.

10. A housing as claimed in claim 1 wherein said first surface is contoured.

11. A housing as claimed in claim 10 wherein said first surface has a plurality of exterior ridges.

12. A housing as claimed in claim 11 wherein each of said ridges has at least one edge with a sharp corner.

13. A housing as claimed in claim 1 wherein said second surface is polished.

* * * * *